United States Patent [19]

Harris

[11] Patent Number: 5,545,147
[45] Date of Patent: Aug. 13, 1996

[54] ANTI-BACKUP IMPROVEMENT FOR HYPODERMIC SYRINGES

[75] Inventor: Dale C. Harris, Fairland, Ind.

[73] Assignee: Eli Lilly and Company, Indianapolis, Ind.

[21] Appl. No.: 963,815

[22] Filed: Oct. 20, 1992

[51] Int. Cl.⁶ ........................................ A61M 5/00
[52] U.S. Cl. .................... 604/209; 604/208; 604/211
[58] Field of Search .................... 604/207–211, 186, 604/169, 232

[56] References Cited

U.S. PATENT DOCUMENTS

| | | | |
|---|---|---|---|
| 3,002,517 | 12/1959 | Pitton . | |
| 3,232,117 | 2/1966 | Gilmont . | |
| 3,613,952 | 10/1971 | Gilmont | 222/43 |
| 3,815,785 | 6/1974 | Gilmont | 222/46 |
| 3,884,230 | 5/1975 | Wulff . | |
| 4,096,751 | 6/1978 | Withers et al. . | |
| 4,275,729 | 6/1981 | Silver et al. . | |
| 4,367,739 | 1/1983 | Le Veen et al. . | |
| 4,395,921 | 8/1983 | Oppenlander . | |
| 4,413,760 | 11/1983 | Paton | 222/309 |
| 4,475,905 | 10/1984 | Himmelstrup | 604/208 |
| 4,498,904 | 2/1985 | Turner et al. | 604/211 |
| 4,592,745 | 6/1986 | Rex et al. | 604/211 |
| 4,710,179 | 12/1987 | Haber et al. | 604/211 |
| 4,865,591 | 9/1989 | Sams | 604/186 |
| 4,883,472 | 11/1989 | Michel | 604/208 |
| 4,936,833 | 6/1990 | Sams | 604/232 |
| 4,973,318 | 11/1990 | Holm et al. | 604/208 |
| 5,092,842 | 3/1992 | Bechtold et al. | 604/135 |
| 5,112,317 | 5/1992 | Michel | 604/208 |
| 5,114,406 | 5/1992 | Gabriel et al. | 604/136 |

FOREIGN PATENT DOCUMENTS

| | | | |
|---|---|---|---|
| 268191 | 5/1988 | European Pat. Off. . | |
| 327910 | 8/1989 | European Pat. Off. . | |
| 338806 | 10/1989 | European Pat. Off. . | |
| 450905 | 10/1991 | European Pat. Off. . | |
| 496141 | 7/1992 | European Pat. Off. . | |
| 2612782 | 9/1988 | France | 604/207 |
| 250467 | 10/1987 | German Dem. Rep. . | |
| 1632032 | 11/1977 | Germany . | |
| 3031830 | 3/1982 | Germany . | |
| 8804656 U | 9/1988 | Germany . | |
| WO87/02895 | 5/1987 | WIPO . | |
| WO88/07874 | 10/1988 | WIPO . | |
| 8907463 | 8/1989 | WIPO | 604/209 |
| WO91/14467 | 10/1991 | WIPO | A61M 45/315 |

*Primary Examiner*—C. Fred Rosenbaum
*Assistant Examiner*—V. Alexander
*Attorney, Agent, or Firm*—Douglas J. Taylor

[57] ABSTRACT

The present invention provides an improved device for preventing the backing up of a nut on a threaded piston rod in the barrel of a hypodermic syringe at the end of dose administration from such syringe. The preferred device is a pawl mounted on the end of a flexible arm of a nut which cooperates with slots on the inside of a syringe barrel. The nut also has an incline surface at the end which mates with an incline surface in the barrel end. The mating of these surfaces at the end of dose administration forces the pawl into a slot, thereby preventing rotation of the nut in the wrong direction and the concurrent movement of the nut up the piston rod associated therewith.

3 Claims, 3 Drawing Sheets

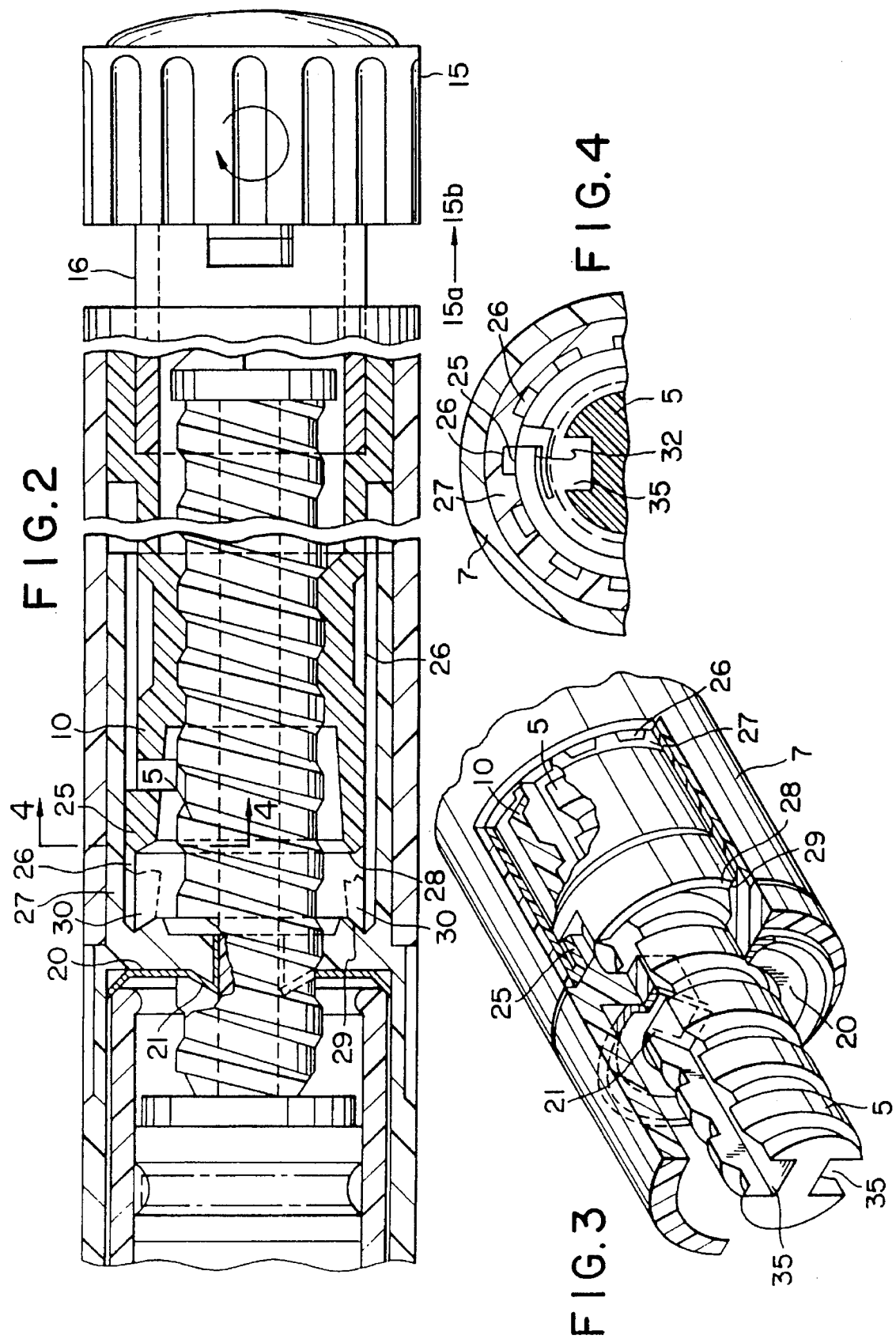

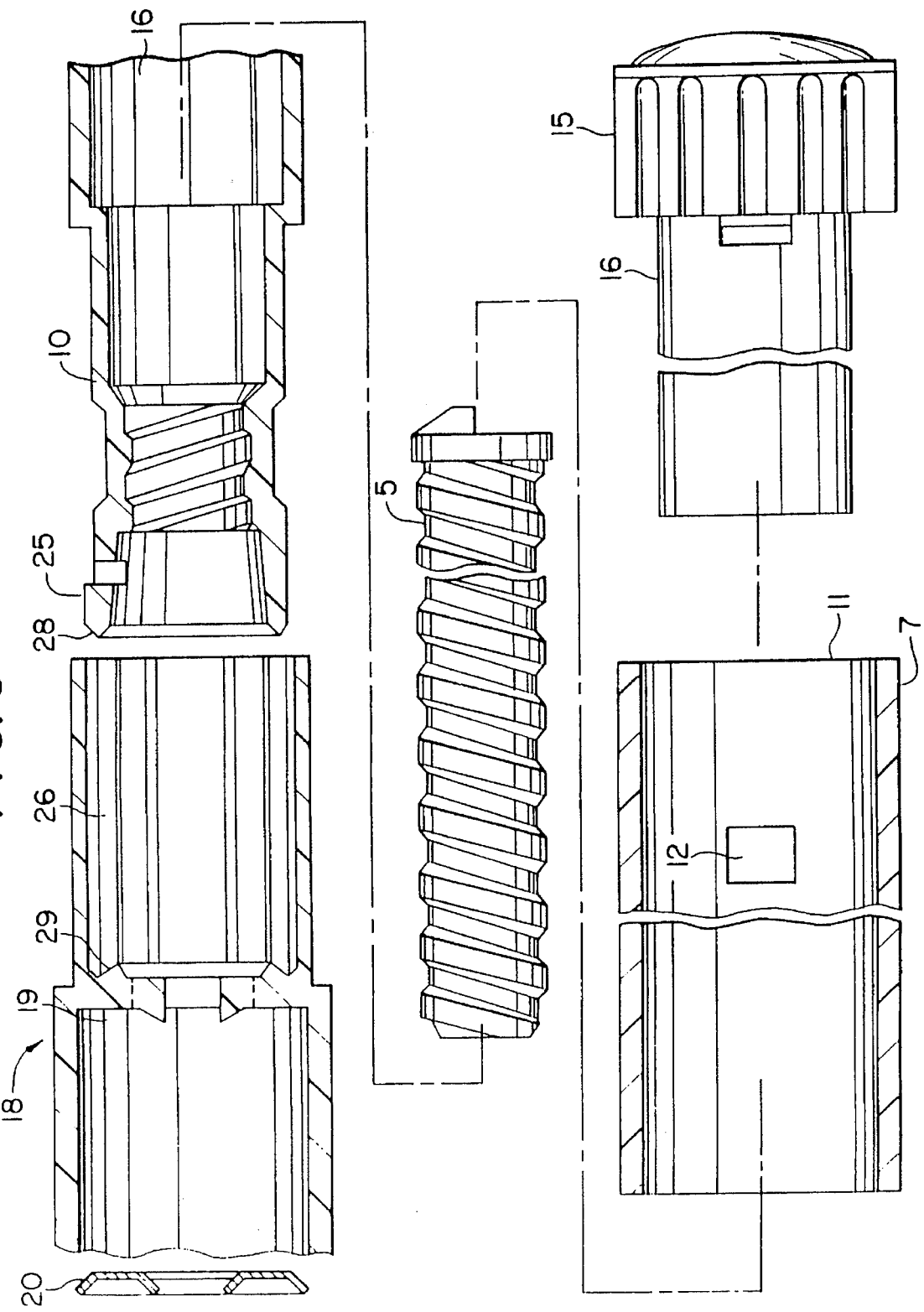

ANTI-BACKUP IMPROVEMENT FOR HYPODERMIC SYRINGES

BACKGROUND OF THE INVENTION

1. Field of the Invention

This invention is in the field of devices for injecting precisely metered doses of pharmaceutical agents. The invention particularly relates to a hypodermic syringe having the same general appearance as a pen or mechanical pencil which is specifically adapted to provide for multiple measured doses of agents such as insulin or human growth hormone.

2. Description of the Prior Art

Diabetics and others frequently find themselves in situations where the assistance of a health professional is unavailable to administer a subcutaneous or intramuscular injection of measured amount of a liquid agent. In such situations such persons need to have a low-cost syringe which does not require the assistance of a health professional to achieve the desired measure of accuracy. It is often the case that such persons require more than one dose per day, each dose being of a somewhat different volume. Dispensers of this general type are known which are the general appearance of a pen or mechanical pencil. The dispenser is typically large enough to hold several such doses, yet it is small enough to fit conveniently in one's pocket or purse. Examples of such devices are to be found in U.S. Pat. Nos. 4,973,318; 4,413,760; 4,498,904; 3,613,952; 4,475,905; 4,883,472; and 4,592,745. Additional examples are show in PCT International Publications WO 87/02895; WO 88/07874; WO 82/02662; PCT CH 86/00151; PCT DK 88/0064.

In devices of this class, a container of the liquid is generally provided having a closed first end adapted to be penetrated by a needle assembly so as to permit the liquid in the container to pass out the injection. The second end of the container is generally closed by a piston. To prevent tampering or reuse of the liquid container, the piston is generally designed such that a pushing force can be applied to the piston to reduce the liquid-holding volume of the container, but no feature is presented which would be suitable for pulling on the piston so as to enlarge the liquid-holding volume of the container.

An elongated member in the nature of a plunger rod is received within the housing for exerting a force on the piston closing the second end of the container. A means is provided for measuring the distance which the plunger rod travels to determine the decrease in volume of the liquid container which causes the dispensing of the liquid within the container. It has generally been recognized that the dispenser should have some feature which would allow the rod to only travel in a single direction toward the piston thereby preventing any action on the part of the rod which might permit an enlargement of the volume of the liquid container. A safety cover is generally provided over a needle assembly attached to the closed end of the container.

While the prior art pen-style syringes have met with some success, certain shortcomings have also been observed. In some prior art pens it is difficult to be sure that after a dose has been administered there is not a back-up which unintentionally alters the length of the piston stroke for the next dose.

SUMMARY OF THE INVENTION

The present invention provides an anti-backup device which prevents the nut from moving up the threaded piston at the end of the dose by rotating in the opposite direction of that in which the nut moves up the position to set the new dose. In this way, it is assured that movement of the nut up the threaded piston is due to rotating the dose knob in the proper direction.

The invention provides an improved device for preventing the backing up of a nut on a threaded piston rod in the barrel of a hypodermic syringe at the end of a dose comprising a pawl means on the nut which cooperates with a rachet means within the barrel and a means on the nut which cooperates with a means in the barrel for forcing the pawl means into the rachet means at the end of the dose to prevent rotation of the nut in the opposite direction to the dose setting direction.

This invention encompasses an improved device for preventing the backing up of a nut on a threaded piston rod in the barrel of a hypodermic syringe at the end of a dose comprising a pawl on the end of the nut which cooperates with slots on the inside of the syringe barrel of the hypodermic syringe to permit the nut to move up the threaded piston rod to set the dose and a first surface at the end of the nut which cooperates with a second surface in the barrel at the end of the dose to drive the pawl into a slot in the barrel and prevent rotation of the nut in the direction opposite to the dose setting direction.

Preferably, the pawl is mounted on a flexible arm integrally molded at the end of the nut and the first surface at the end of the nut is an incline plane and the second surface in the barrel is an incline plane mating with the first incline plane wherein the mating of the incline planes at the end of the dose prevent the flexible pawl arm from moving inward and maintains the pawl in a slot in the barrel and thereby prevents rotation in the wrong direction.

BRIEF DESCRIPTION OF THE DRAWINGS

FIG. 2 is a sectional view of the anti-backup mechanism.

FIG. 3 is a partial sectional view plane a of FIG. 2.

FIG. 4 is a perspective cut-away view of the anti-backup mechanism.

FIG. 5 shows the disassembled parts in mix sectional and top views.

DETAILED DESCRIPTION OF THE INVENTION

Figure 1:
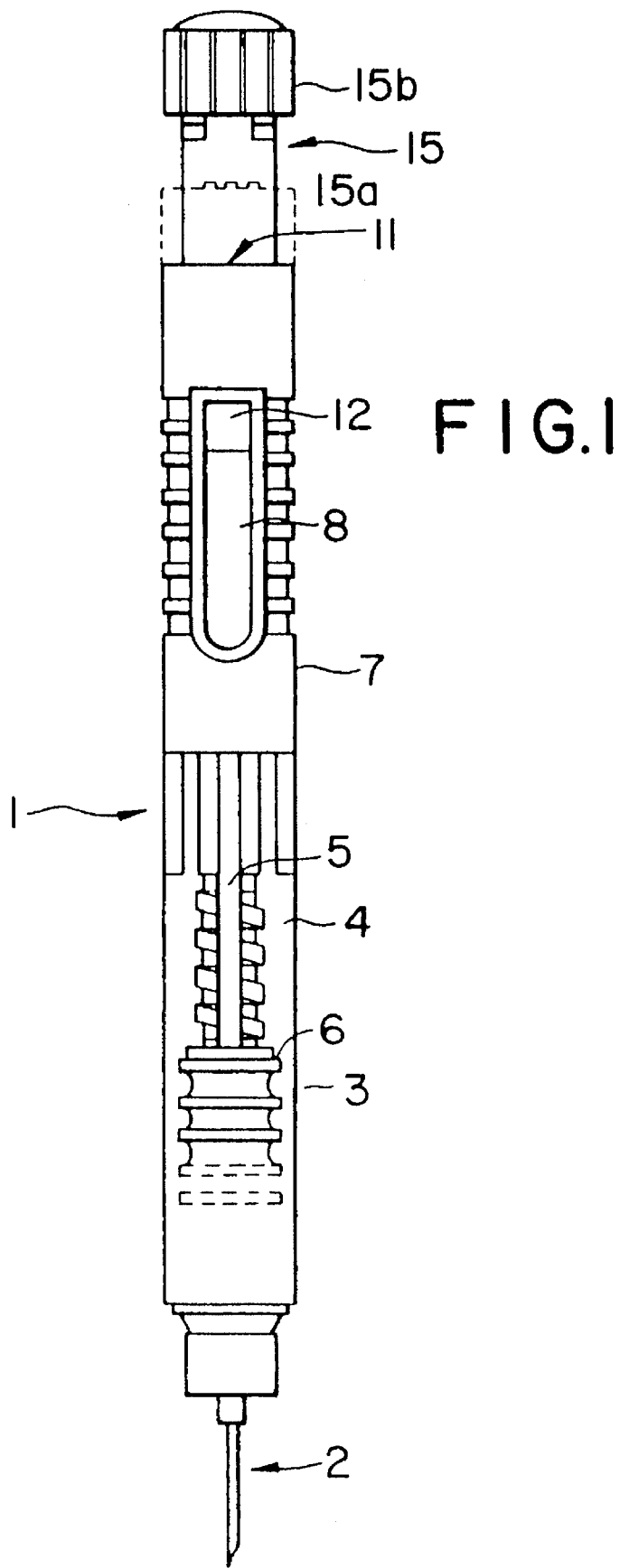
FIG. 1 is a top view of the operative syringe.

The syringe assembly 1 is shown in FIG. 1. The syringe assembly 1 includes a needle assembly 2 which is coupled at the distal end of a syringe 3 which holds within it a container 4 containing the liquid to be administered. A threaded piston rod 5 contacts plunger 6 such that the piston: moves plunger 6 and downward movement forces liquid out of the needle. Overcap 7 is slidably received by the proximal end of the syringe housing 3. A pocket clip 8 is integrally molded as a part of overcap 7. A dose knob 15 fits into an opening 11 at the proximal end of the overcap 7. Rotating dose knob 15 cause an internal nut coupled to the dose knob to ride-up piston 5 and effectively elongates a piston so that the dose knob occupies position 15b which corresponds to a precisely metered dose which can be observed on a scale through window 12. Pushing the dose knob from position 15b to position 15a causes a precisely metered amount of liquid to be ejected through the needle.

The precise description of devices of FIG. 1 as generally explained above is set out in United States Ser. No. 07/361,132, filed Jun. 5, 1989, assigned to the same assignee as this application, now abandoned, the specification of which is incorporated herein by reference. Published European Application number 496,141 published Jul. 29, 1992, is likewise incorporated herein by reference.

Now referring to FIGS. 2–5 which describe the details of the preferred embodiment of this invention.

FIG. 2 illustrates the setting of the dose by turning the dose knob 15 in a clockwise direction. This causes the dose knob to move from position 15(a) to 15(b) and the nut 10 to move on the threaded piston rod 5 in the direction of the dose knob to set the dose. During this operation, the threaded piston rod is held in place by push nut 20 and the prong 21 of the push nut which keeps the threaded piston rod 5 from turning as well as moving toward the dose knob. Also, when the dose knob is turned in the clockwise direction, the pawl 25 on the nut 10 overcomes the slot 26 in the barrel 27.

When the dose knob 15 is pushed to deliver the dose, the beveled end of the nut 28 assumes position 30 such that the end of the nut engages the beveled surface of circular inclined plane 29 on the inside of the barrel 27 at the end of dose position. An attempt to rotate the dose knob 15 in a counterclockwise position results in pressure of nut surface 28 against barrel surface 29. The pawl 25 on the nut 10 now moves up the circular incline plane 29 and into the barrel slot 26 to further restrict the backup of the nut 10. The flange 21 on the push nut 20 prevents the threaded piston rod from moving in the direction of the dose knob. Thus, the mating of incline planes at the end of the nut and in the barrel prevents the flexible arm 32 on which the pawl is mounted from flexing inward and drives the pawl into the slot when an attempt to turn the nut counterclockwise is made.

FIG. 3 shows a perspective partial sectional view of the anti-backup improvement. This view shows the threaded piston rod 5 with grooves 35 and the flange 21 of push nut 20 which prevents the threaded piston rod from turning or moving toward the dose knob. FIG. 3 also shows the mating of incline plane surfaces 28 and 29 on the nut and inside the barrel respectively. Also shown is pawl 25 and slots 26 on the inner surface of the barrel 27. The relationship of the nut 10 to the threaded piston rod is also shown.

FIG. 4 shows a partial cross-sectional view of FIG. 2 through plane 4—4. FIG. 4 illustrates how pawl 25 is mounted on a flexible arm 32 so that it springs in and out of slots 26 in barrel 27 when the nut is rotated to set the dose. The arrow shows the direction of rotation to move the nut up the threaded piston to set the dose. At the end of the dose when dose knob 15 is pushed as far as it will go toward the overcap to deliver the dose the pawl 25 is driven into the slot 26 to prevent the nut from backing up by the interacting of incline planes 28 and 29.

FIG. 5 shows disassembled components: threaded piston rod 5, nut 10, slotted barrel 27, push nut 20, dose knob 15, and overcap 7. The cylinder 16 of the dose knob tightly fits into the opening 16 of the nut 10 to effectively become one piece such that when the dose knob is turned, the nut turns. The nut 10 is threaded on the threaded piston rod. The pawl section of the nut 10 is inserted into the slotted barrel 27. The end of the threaded piston rod is set in the push nut 20 which is located at position 19 in the barrel. Overcap 7 has opening 11 for receiving cylinder 16.

Push nut 20 is made of a metal such as copper, or stainless steel. The other parts are molded plastic parts such as the dose knob, threaded piston rod, nut, slotted barrel, and overcap.

Those skilled in this art will recognize shapes and sizes, and position of surfaces on the nut and in the barrel which will force the pawl into a slot at the end of a dose. Similarly, those skilled in this art will recognize various pawl and rachet combinations and positioning to accomplish the purposes of the invention.

The embodiments of the invention described above are intended to illustrate the invention and not to limit it in spirit or scope.

What is claimed is:

1. An improved device for preventing the backing up of a nut on a threaded piston rod in a barrel of a hypodermic syringe at the end of a dose comprising a pawl means on the nut which cooperates with a rachet means within the barrel and a means on the nut which cooperates with a means in the barrel for forcing the pawl means into the rachet means at the end of the dose to prevent rotation of the nut in the opposite direction to the dose setting direction.

2. An improved device according to claim 1 for preventing the backing up of a nut on a threaded piston rod in the barrel of a hypodermic syringe at the end of a dose comprising a pawl on the end of the nut which cooperates with slots on the inside of the syringe barrel of the hypodermic syringe to permit the nut to move up the threaded piston rod to set the dose and a first surface at the end of the nut which cooperates with a second surface in the barrel at the end of the dose to drive the pawl into a slot in the barrel and prevent rotation of the nut in the direction opposite to the dose setting direction.

3. The improvement of claim 2 wherein the pawl is mounted on a flexible arm and the first surface at the end of the nut is an incline plane and the second surface in the barrel is an incline plane mating with the first incline plane wherein the mating of the incline planes prevent the flexible pawl arm from moving inward and maintains the pawl in a slot in the barrel.

\* \* \* \* \*